(12) United States Patent
Wilson, Jr. et al.

(10) Patent No.: US 7,316,696 B2
(45) Date of Patent: Jan. 8, 2008

(54) LIGATING CLIP WITH INTEGRAL INTERLOCKING LATCH MECHANISM

(75) Inventors: Donald F. Wilson, Jr., Raleigh, NC (US); David N. Fowler, Raleigh, NC (US); Steven J Owens, Loveland, OH (US)

(73) Assignee: Teleflex Medical Incorporated, Limerick, PA (US)

( * ) Notice: Subject to any disclaimer, the term of this patent is extended or adjusted under 35 U.S.C. 154(b) by 542 days.

(21) Appl. No.: 10/763,032

(22) Filed: Jan. 22, 2004

(65) Prior Publication Data

US 2005/0165421 A1      Jul. 28, 2005

(51) Int. Cl.
  *A61B 17/08*   (2006.01)
  *A61B 17/32*   (2006.01)
  *A61M 5/00*    (2006.01)
  *A45D 8/20*    (2006.01)
  *A45D 8/22*    (2006.01)

(52) U.S. Cl. .................. 606/158; 606/151; 606/170; 606/178; 606/179; 604/250; 132/277; 132/278; 132/279

(58) Field of Classification Search ............... 606/151, 606/170, 178, 179, 256, 158; 132/277–279; 604/250

See application file for complete search history.

(56) References Cited

U.S. PATENT DOCUMENTS

| | | | |
|---|---|---|---|
| 3,247,852 A * | 4/1966 | Schneider ............... 606/120 |
| 4,519,392 A | 5/1985 | Lingua |
| 4,834,096 A * | 5/1989 | Oh et al. ................. 606/158 |
| 5,062,846 A * | 11/1991 | Oh et al. ................. 606/158 |
| 5,575,802 A * | 11/1996 | McQuilkin et al. ....... 606/151 |
| 6,716,226 B2 * | 4/2004 | Sixto et al. ............. 606/157 |
| 6,863,675 B2 * | 3/2005 | Wilson, Jr. .............. 606/157 |
| 7,001,412 B2 * | 2/2006 | Gallagher et al. ........ 606/232 |

* cited by examiner

*Primary Examiner*—(Jackie) Tan-Uyen Ho
*Assistant Examiner*—Melissa Ryckman
(74) *Attorney, Agent, or Firm*—Baker Hostetler LLP (57) ABSTRACT

A polymeric, surgical clip having first and second curved legs joined at their proximal ends by a flexible hinge section and movable from an open position to a closed position for clamping a vessel between curved opposing inner surfaces. The first leg terminates at its distal end in a female locking member comprising a resilient inwardly turned hook having a recess in the mouth of the hook, and the second leg member terminates in a male locking member complimentary to the female locking member and comprising a detent such that when the first and second leg members are moved from an open position to a closed position about the hinge section the hook member will deflect about the distal end of the second leg member thereby engulfing the male locking member in the mouth of the hook and matingly engaging the detent in the recess thereof, thus securely locking the clip in the closed position. The locking feature provides greater closure security to the clip when clamping large diameter or uncompressible tissue.

9 Claims, 9 Drawing Sheets

LIGATING CLIP WITH INTEGRAL INTERLOCKING LATCH MECHANISM

TECHNICAL FIELD

Disclosed herein are surgical clips, and more particularly ligating clips with integral interlocking latch mechanisms to facilitate securely locking the surgical clip in a closed position. Yet more particularly, disclosed herein is an improved surgical ligating clip that is provided with a female locking member on one leg and a male locking member on the other leg, wherein the female locking member comprises a resilient hook defining a recess within the mouth of the hook and the male locking member comprises at least one detent. The female and male locking members are positioned such that when the leg members are moved from an open position to a closed position, the resilient hook is urged open to receive the male locking member, while the recess also receives the detent, providing an improved locking feature to more securely lock the clip in the closed position.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue even after hemostasis or occlusion occurs. At some point thereafter, the clip can be removed by using a separate instrument dedicated for that purpose, i.e., a clip removal instrument.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood in which a forceps-type applier having conformal jaws is used to grip and maintain alignment of the clip during deformation. Such appliers may additionally dispense a plurality of clips for sequential application, as disclosed in U.S. Pat. No. 4,509,518 to McGarry et al.

With the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as the plastic clip cannot be permanently deformed for secure closure around a vessel or other tissue, latching mechanisms have been incorporated into the clip design to establish closure conditions and to secure against re-opening of the vessel. For example, well known polymeric clips are disclosed in U.S. Pat. No. 4,834,096 to Oh et al. and U.S. Pat. No. 5,062,846 to Oh et al., both of which are assigned to the assignee of the present invention. These plastic clips generally comprise a pair of curved legs joined at their proximal ends with an integral hinge or heel. The distal ends of the curved legs include interlocking latching members. For example, the distal end of one leg terminates in a lip or hook structure into which the distal end of the other leg securely fits to lock the clip in place.

The distal ends of the clips taught by Oh et al. also include lateral bosses that are engaged by the jaws of the clip applier. A clip applier specifically designed for asymmetric plastic clips is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg. A clip applier designed for use with asymmetric plastic clips in an open (i.e., non-endoscopic) surgical procedure is disclosed in U.S. Pat. No. 5,100,416 to Oh et al., also assigned to the assignee of the present invention.

In addition to compatibility with sophisticated diagnostic techniques, asymmetric clips have other advantages over symmetric clips. For example, because asymmetric clips are formed from polymeric materials, the mouths of asymmetric clips can generally be opened wider than the mouths of symmetric clips. This allows a surgeon to position the clip about the desired vessel with greater accuracy. In addition, a clip of the type described in the aforementioned U.S. Pat. Nos. 4,834,096 and 5,062,846 can be repositioned before locking the clip on the vessel or before removing the clip from the vessel, in a process referred to as "approximating" the clip.

Although plastic ligating clips are well known in the surgical arena and improvements have been made to the ligating clips including providing an interlocking latch member as described above (see also, for example, the aforementioned Oh et al. U.S. Pat. Nos. 4,834,096 and 5,062,846), the latching mechanisms of the prior art plastic ligating clips are limited in the amount of force that can be applied against them. In certain circumstances, when excess force is applied to the latch mechanism, the latch mechanism may fail and the clip inadvertently open. For example, when large diameter, non-compressible tissue such as ligaments require clamping, ligating clips with the simple prior art latching mechanism may not be able to maintain the tension required to keep the clamp closed. Thus, surgeons may benefit from a clip having a more secure interlocking latch when the tissue to be clamped will place excessive force on the latch mechanism. Therefore, there is believed to be a long-felt need for an improved polymeric surgical ligating clip with an integral interlocking latch mechanism to provide an increased binding capacity so as to be particularly well suited for use in clamping large or non-compressible tissue such as ligaments and the like. The present invention is believed to provide such an improved surgical clip.

BRIEF SUMMARY

In accordance with the embodiments disclosed herein, a polymeric surgical clip is provided of the type comprising first and second legs joined at their proximal ends by a flexible hinge section. The hinge section has a continuous concave inner surface and a continuous convex outer surface. Each leg member has a vessel clamping inner surface and an opposite outer surface, and the vessel clamping inner surface of one leg is in opposition to the vessel clamping inner surface of the other leg. The first leg terminates at its distal end in a female locking member comprising a resilient inwardly turned hook defining a recess within the mouth of the hook, and the second leg member terminates at its distal end in a male locking member comprising at least one detent. The female and male locking members are complimentary to one another and positioned such that when the first and second legs are moved from an open position to a closed position about the hinge section, the hook member deflects about the male locking member and is urged open to receive the detent of the male locking member in the recess of the female locking member to lock the clip in a closed position. The clip may preferably be provided with at least one detent having an inwardly turned lip extending generally toward the hinge section for further lockingly engaging the detent to the recess in the mouth of the hook, thus providing a third locking feature.

In the preferred embodiment, the surgical clip has a female locking member with a bifurcated recess and the male locking member has two outwardly extending spaced-apart detents that each engages a respective one of the two halves of the bifurcated recess. The bifurcated recess is defined by a gusset projecting outward from the mouth of the hook that provides structural support to the hook of the female locking member so that the hook is not excessively deformed by initial contact with the male locking member when the clip is closed.

Further in the preferred embodiment, the inner vessel-clamping surface of the first leg has a concave radius of curvature and the outer surface has a convex radius of curvature between the hinge section and the distal end. In the same embodiment, the inner vessel-clamping surface of the second leg has a convex radius of curvature and the outer surface has a concave radius of curvature between the hinge section and the distal end.

Further in the preferred embodiment, the surgical clip comprises a pair of bosses joined to opposite sides of the first leg between the hinge section and the distal end of the first leg. A portion of the pair of bosses extend beyond the outer surface of the first leg to form a bridge section. Another pair of bosses is also joined to opposite sides of the second leg, at its distal end. The bosses on the second leg can each have a sharp tissue-penetrating tooth extending therefrom and toward the first leg.

Still further in the preferred embodiment, at least one of the inner surfaces of the clip comprises a plurality of protrusions extending from the inner surface, for providing improved vessel retention during and following closure of the clip. Preferably, both of the inner surfaces comprise the plurality of protrusions.

The surgical clip disclosed herein is most suitably made of polymeric material and accordingly minimizes interference with high technology diagnostic modalities such as CAT SCAN, MRI and MRS. At the same time, the clip is nearly as small as comparable metal clips while maintaining sufficient strength and possessing a high degree of security in the clip's latching mechanism. The surgical clip is configured to provide a secure means of handling an application to avoid premature release from the applier of the clip.

It is therefore an object of the present invention to provide a polymeric surgical clip capable of occluding a vessel or fastening other tissue by being securely locked in a closed position to assure it will not release maturely, even when the secured tissue is large in diameter or generally non-compressible.

Some of the objects of the invention having been stated hereinabove, other objects will become evident as the description proceeds when taken in connection with the accompanying drawings as best described hereinbelow.

DETAILED DESCRIPTION OF THE INVENTION

Referring now to FIGS. 1-7, one example is illustrated of an asymmetric surgical clip with an improved latching mechanism generally designated 12, which is suitable for use as disclosed herein. Clip 12 and others of similar design are useful as hemostatic clips that can be latched around a vessel to ligate the vessel and thereby stop or reduce the flow of fluid through the vessel. Clip 12 is also useful for clamping other types of tissue as well. Clip 12 is particularly useful for clamping non-compressible tissue, such as ligaments, and other large diameter tissue, such as large vessels that cannot be clamped using traditional metal clips or other polymeric clips with known latching mechanisms.

Clip 12 can be constructed from any suitable biocompatible material, such as certain metals and polymers. However, the presently disclosed subject matter is particularly suitable for practice with polymeric clips. Thus, clip 12 preferably comprises a one-piece integral polymeric body formed from a suitable strong biocompatible engineering plastic such as the type commonly used for surgical implants. Examples include acetal polyoxymethylene (POM), polyethylene terephthalate (PET), polybutylene terephthalate (PBT), polyoxymethylene, or other thermoplastic materials having similar properties that can be injection-molded, extruded or otherwise processed into like articles.

Figure 1:
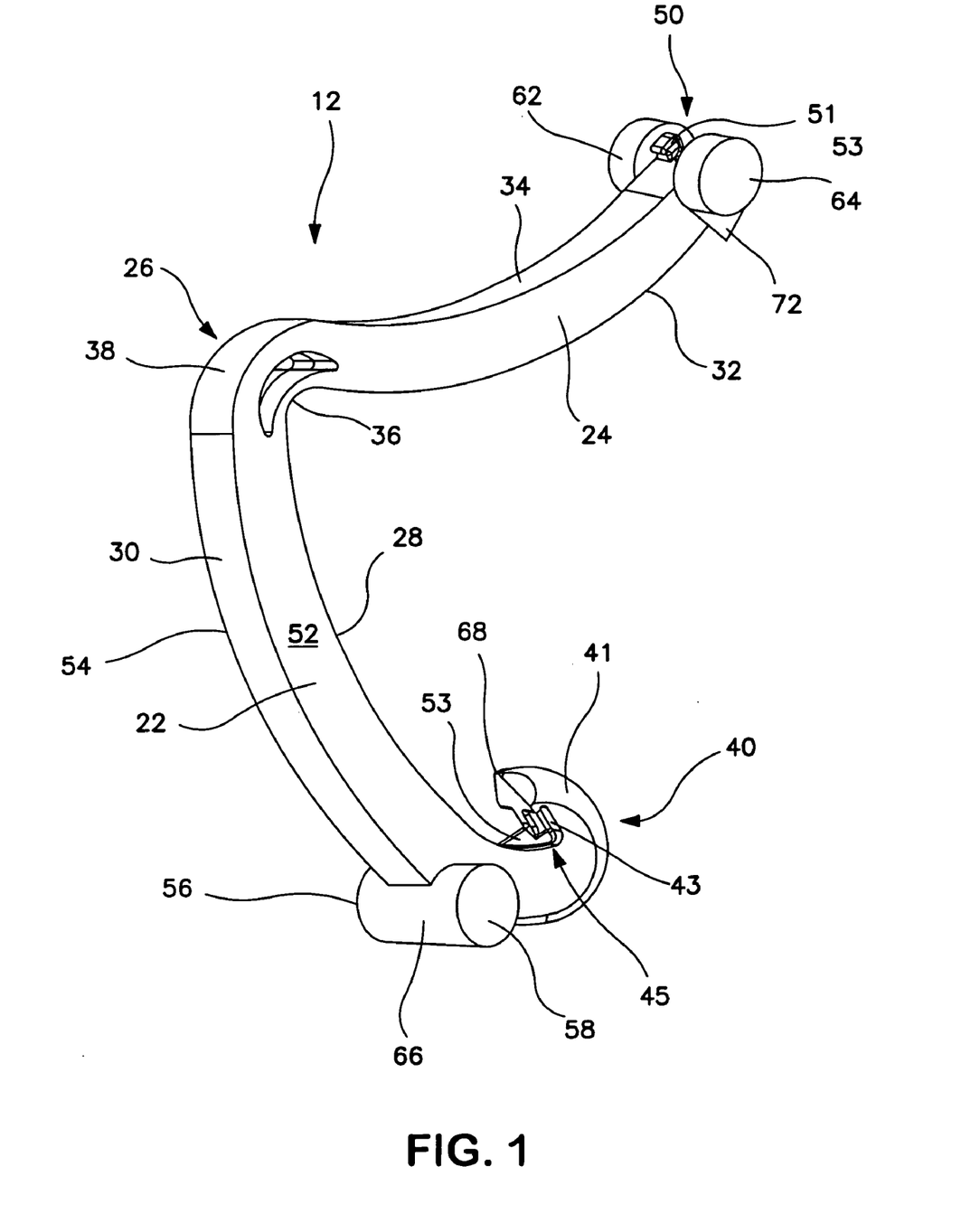
FIG. 1 is a perspective view of the improved surgical ligating clip of the present invention.
Figure 2:
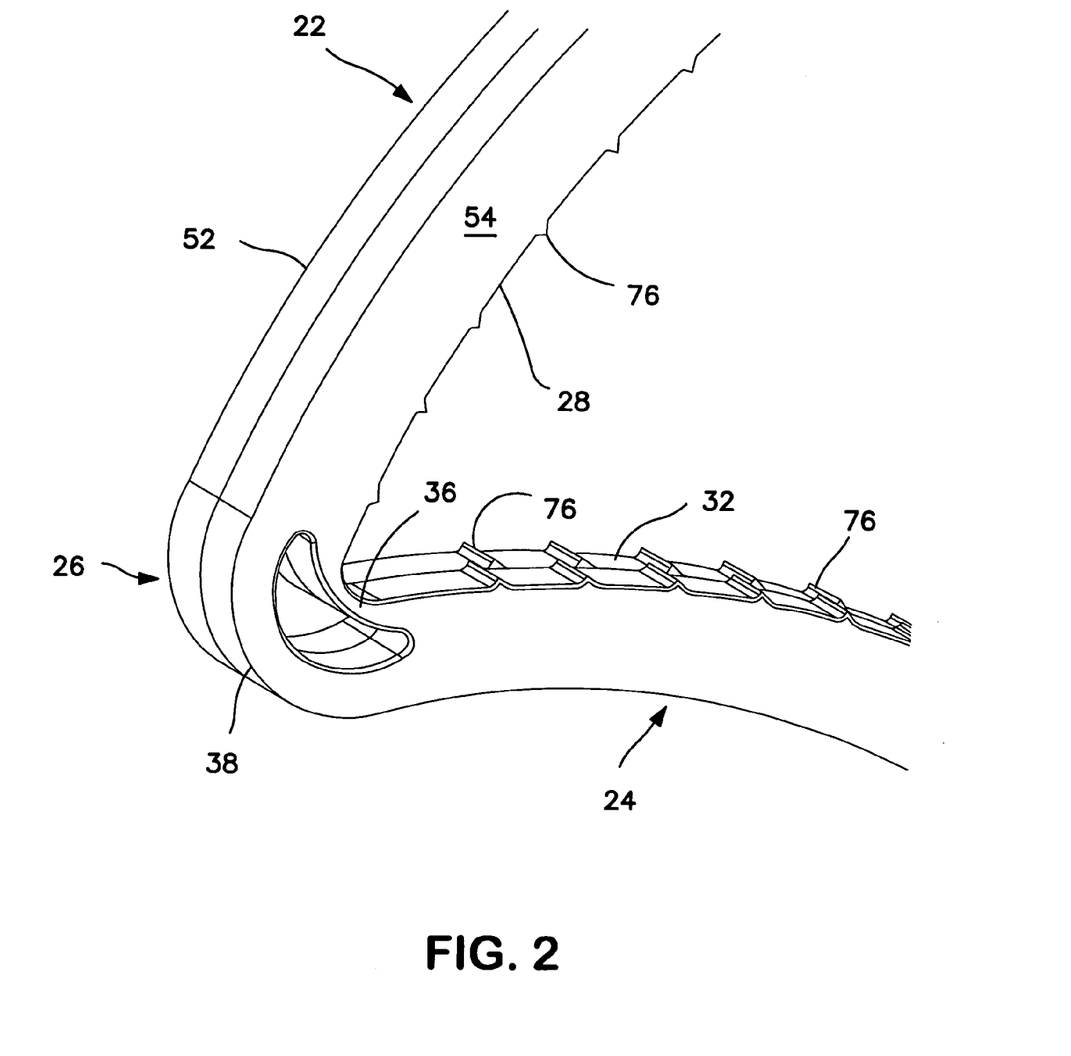
FIG. 2 is an enlarged perspective view of the surgical ligating clip showing the hinge section and proximal ends of the first and second legs in detail including the plurality of protrusions on the inner surface of one leg.

As best shown in FIG. 1, the body of clip 12 comprises a first or outer leg, generally designated 22, and a second or inner leg, generally designated 24. First and second legs 22 and 24 are joined at their proximal ends by an integral flexible hinge section, generally designated 26. First and second legs 22 and 24 have complementary arcuate profiles. Thus, first leg 22 has a concave inner vessel-clamping surface 28 and a convex outer surface 30, and second leg 24 has a convex inner vessel-clamping surface 32 and a concave outer surface 34. Convex inner surface 32 of second leg 24 and concave inner surface 28 of first leg 22 have substantially matching radii of curvature, as shown in FIG. 2. Flexible hinge section 26 has a continuous concave inner surface 36 and a continuous convex outer surface 38. Concave inner surface 36 of hinge section 26 joins concave inner surface 28 of first leg 22 and convex inner surface 32 of second leg 24. Convex outer surface 38 of hinge section 26 joins convex outer surface 30 of first leg 22 and concave outer surface 34 of second leg 24.

Figure 3:
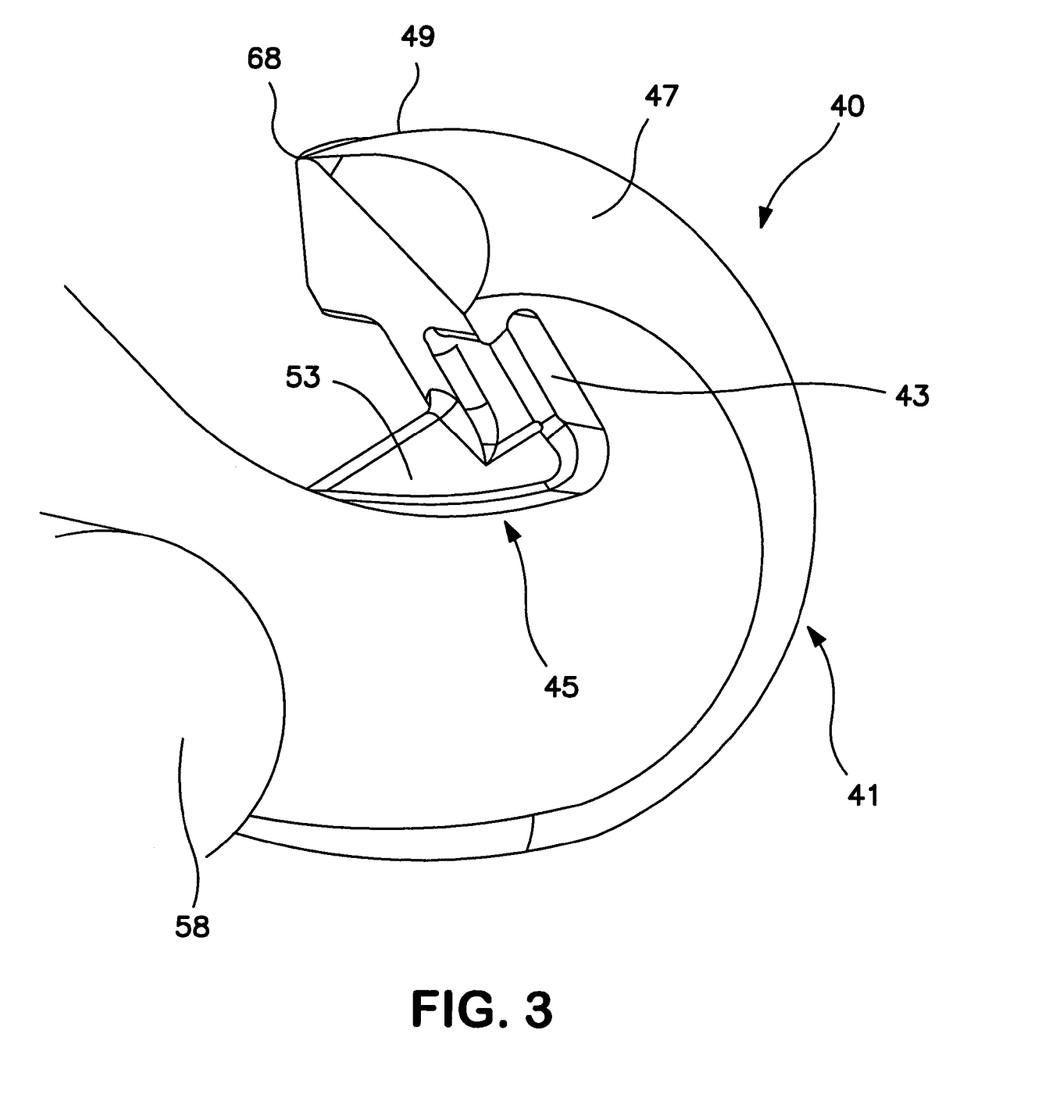
FIG. 3 is an enlarged fragmentary perspective view of the female locking member on the first leg of the surgical ligating clip showing the recess and gusset in detail.
Figure 4:
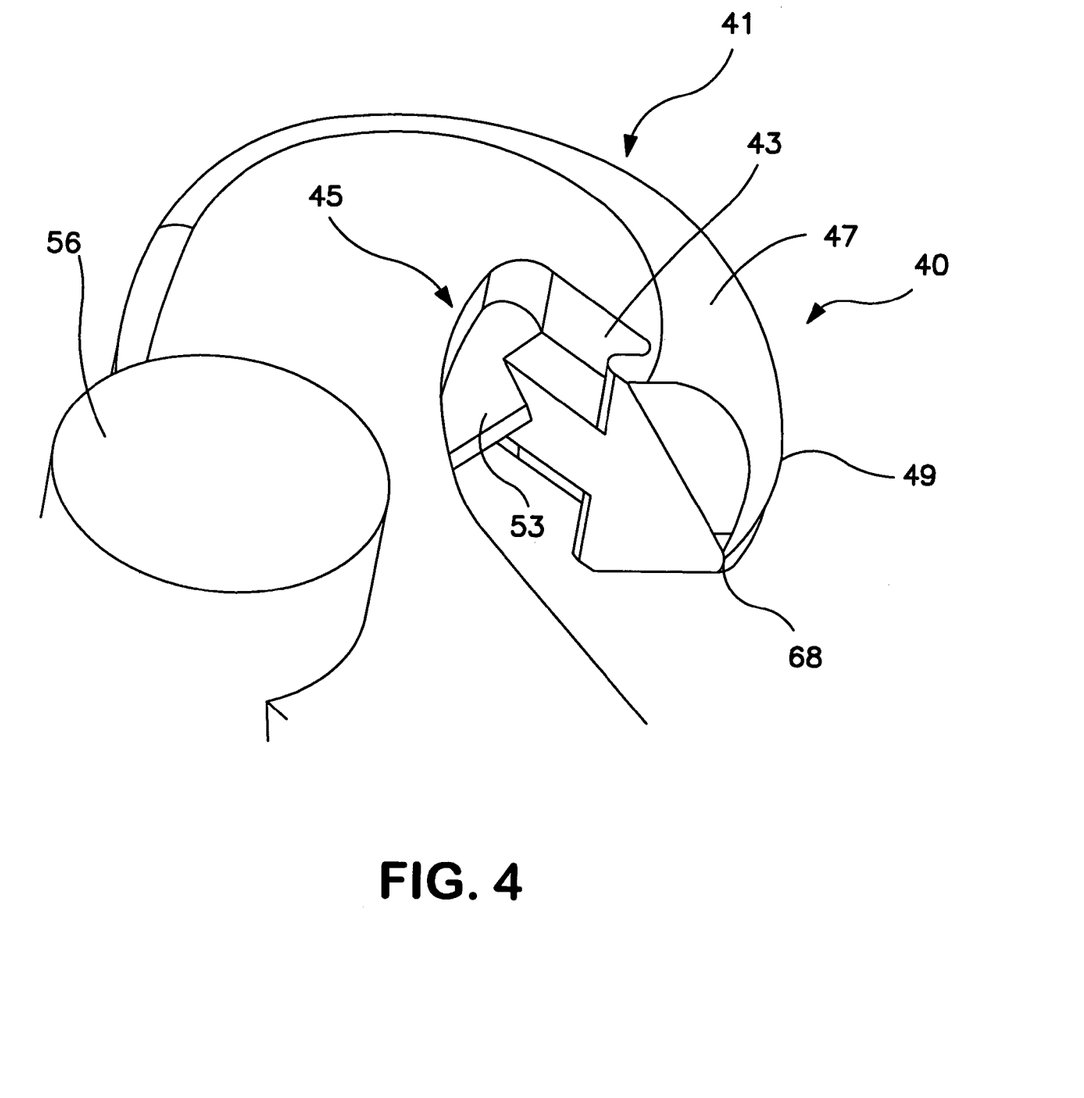
FIG. 4 is another enlarged fragmentary perspective view of the female locking member on the first leg of the surgical ligating clip.

First leg 22 terminates in a female locking member 40, having a C-shaped hook 41 at its distal end. As best shown in FIGS. 3 and 4, female locking member 40 is distally curved inwardly toward hinge section 26 to form resilient inwardly turned hook 41. A recess 43 is positioned within the mouth 45 of hook 41, adjacent the distal end of hook 41. Hook 41 and recess 43 are adapted for releasably engaging male locking member 50 at the end of second leg 24 in the course of compressing clip 12 into a latched or locked position around a vessel, ligament or other tissue, as described hereinbelow in greater detail. Optionally, the top surface of female locking member 40 (see FIGS. 3 and 4) comprises two convex surfaces 47 that come together to define a sharp crest-like cutting edge 49 to facilitate cutting through connective tissue adjacent a vessel or other tissue during latching of the clip therearound.

As best shown in FIGS. 3 and 4, hook 41 further comprises a brace or gusset 53 for strengthening the arch of hook 41. As clip 12 is moved to the closed position, male locking member 50 first contacts female locking member 40 at the crest of hook 41, thereby applying compressive force to hook 41. If excessive friction occurs at contact spots due to unique local conditions, the compressive force will increase sufficiently to collapse the arch of hook 41. If hook 41 collapses, mouth 45 closes, and male locking member 50 is prevented from entering female locking member 40, effectively preventing locking of clip 12. Gusset 53 strengthens hook 41 sufficiently to prevent its collapse in situations of high compressive force during closure of clip 12. In the preferred embodiment described herein, gusset 53 extends into recess 43 and effectively bifurcates recess 43 (see FIGS. 3 and 4).

Figure 5:
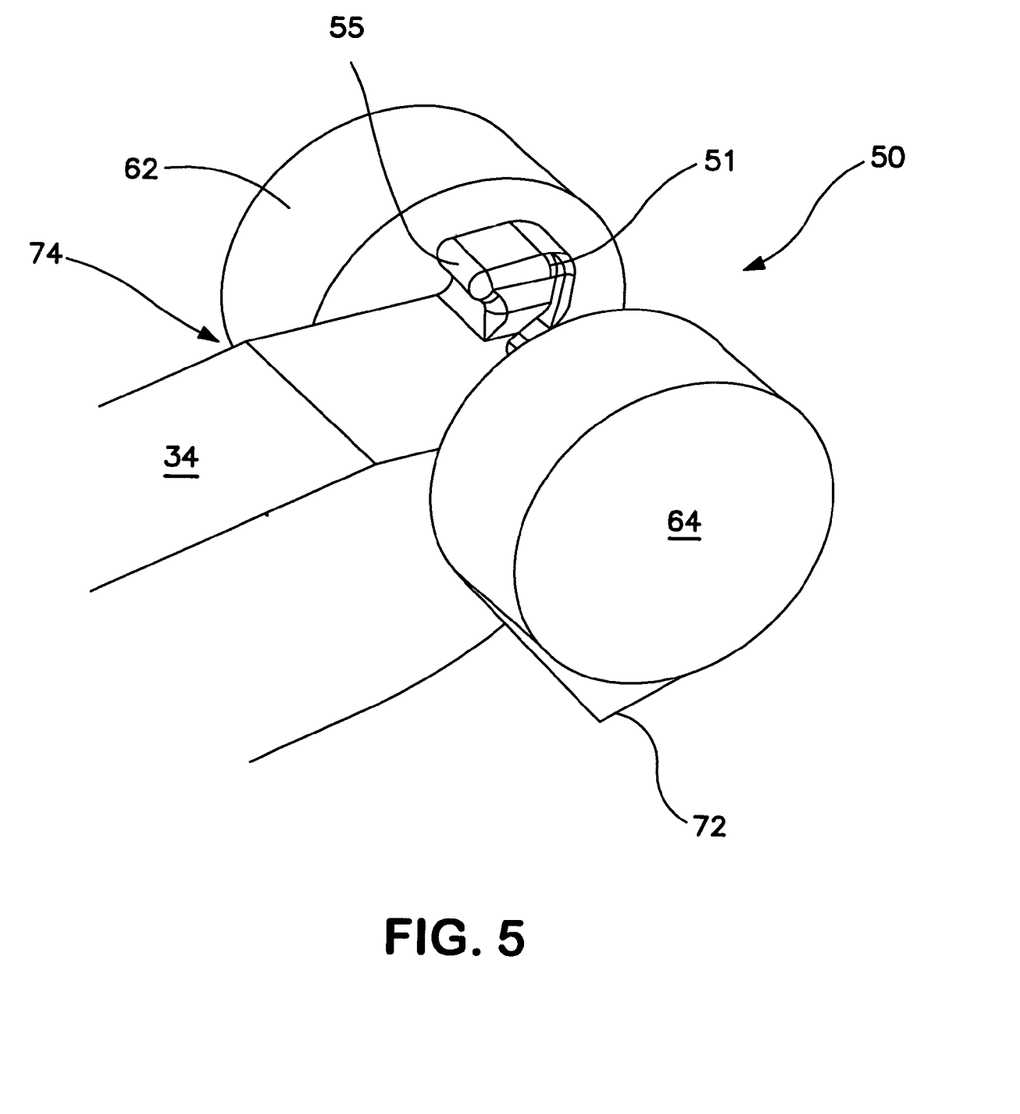
FIG. 5 is an enlarged fragmentary perspective view of the male locking member on the second leg of the surgical ligating clip showing the detent and inwardly turned lip thereof in detail.
Figure 6:
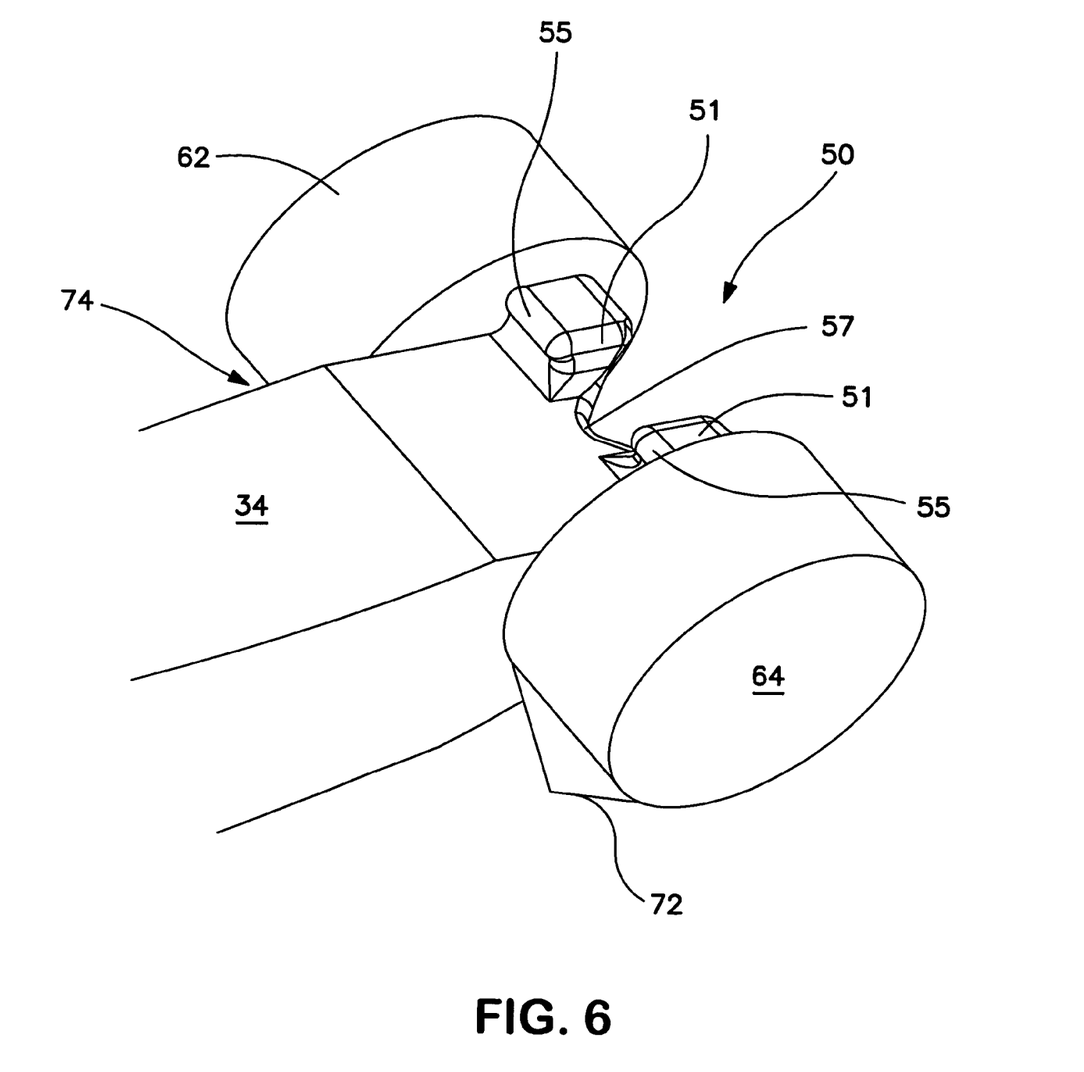
FIG. 6 is another enlarged fragmentary perspective view of the male locking member on the second leg of the surgical ligating clip.

As best shown in FIGS. 5 and 6, second leg 24 terminates in male locking member 50 at its distal end. Extending outward from male locking member 50 on concave outer surface 34 at the distal end of second leg 24 are two detents 51. Detents 51 are positioned to matingly engage recess 43 of female locking member 40 when clip 12 is moved to a closed position, thus securely locking clip 12 in the closed position. To further ensure clip 12 remains in the closed and locked position, detents 51 further each comprise an inwardly turned lip 55 that enhances the locking engagement of recess 43 of female locking member 40. Although the invention contemplates that a single detent 51 could be used, detents 51 most suitably are a plurality of detents, preferably two detents 51 separated by a groove 57, as best shown in FIGS. 5 and 6. In this preferred embodiment, recess 43 is bifurcated with each half of the bifurcated recess engaging one of detents 51. Groove 57 functions to guide sharp tip 68 on female locking member 40 over male locking member 50 as clip 12 is moved to the closed position. Positioning sharp tip 68 facilitates proper locking engagement of male locking member 50 with female locking member 40. When clip 12 is in the closed position, gusset 53 of female locking member 40 nestles within groove 57 of male locking member 50.

As best shown in FIG. 2, which is a view directed into the open convex side of clip 12, clip 12 also comprises opposing side surfaces 52 and 54. Typically, the body of clip 12 has a constant thickness between side surfaces 52 and 54. Both first and second legs 22 and 24 have a plurality of protrusions or teeth 76 extending from their respective inner surfaces 28 and 32, and in a preferred embodiment, extending completely across inner surfaces 28 and 32 until meeting side surfaces 52 and 54. These latter features are designed to engage the tissue of the vessel being clamped and assist in preventing the vessel from sliding laterally or longitudinally during or following clip closure. It will be noted, however, that other clips equally suitable for use in conjunction with the invention do not contain such features.

Adjacent to the distal end of first leg 22 and immediately inwardly of female locking member 40, a pair of cylindrical bosses 56 and 58 are formed coaxially on the opposed lateral surfaces of first leg 22. In the illustrated example of clip 12, a bridge section 66 couples bosses 56 and 58 together. As evident in FIG. 1, bosses 56 and 58 project outwardly beyond convex outer surface 30 of first leg 22. Referring still to FIG. 1, at the distal end of second or inner leg 24, another pair of cylindrical bosses 62 and 64 is formed coaxially on the opposed lateral surfaces of inner leg 24 at tip section 42. As best shown in FIGS. 5 and 6, bosses 62 and 64 of second leg 24 extend forwardly beyond male locking member 50.

Clip Closure

Figure 7:
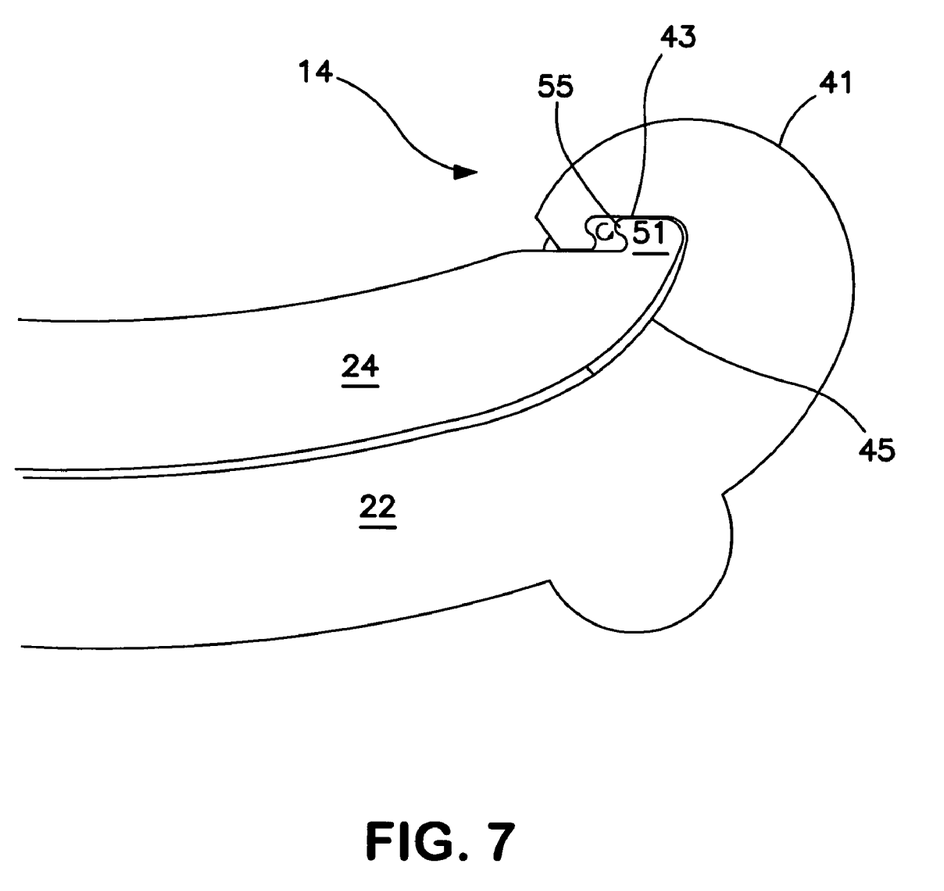
FIG. 7 is a vertical cross-sectional view of the surgical ligating clip in the closed position showing the latching mechanism engaged.

In the practice of ligating a vessel as understood by persons skilled in the art, clip 12 is designed to be compressed into a latched or locked position around the vessel through the use of an appropriate clip applicator instrument, such as the type described in U.S. Pat. No. 5,100,416 and shown in FIGS. 8A through 8C. The clip applicator instrument 120 engages bosses 56, 58, 62 and 64 of clip 12 and pivots bosses 56, 58, 62 and 64 inwardly about hinge section 26. This causes first and second legs 22 and 24 to close around the vessel, ligament, or similar tissue with convex inner surface 32 of second leg 24 and complementary concave inner surface 28 of first leg 22 contacting the outer wall of the vessel or similar tissue. Male locking member 50 of second leg 24 then begins to contact female locking member 40. Further pivotal movement by the applicator instrument longitudinally elongates first leg 22 and hook 41 of female locking member 40 is deflected by initial contact with male locking member 50, urging hook 41 open and allowing male locking member 50 to enter mouth 45 of female locking member 40, thereby aligning detents 51 with bifurcated recess 43. Upon release of the applicator instrument, detents 51 snap into and are matingly seated in bifurcated recess 43. Simultaneously, resilient hook 41 is released from its outwardly flexed position, returning to its normal inwardly turned conformation, and consequently engulfing male locking member 50. At this point, clip 12 is in its securely closed and latched position, as best shown in FIG. 7. In the latched position, male locking member 50 is engaged in mouth 45, and detents 51 are matingly engaged with bifurcated recess 43, thereby providing a latching mechanism and securely clamping a designated vessel or other tissue between concave inner surface 28 and convex inner surface 32.

The interlocking double latching mechanism 14 discussed above, wherein hook 41 engulfs male locking member 50 and detents 51 matingly engage recess 43, is advantageous over the prior art clip devices for its added security of closure. Further, latching mechanism 14 secures tighter than both traditional metal clips and polymeric clips of the prior art with simple latching mechanisms. Therefore, clip 12 with latching mechanism 14 is superior for clamping vessels with large diameters and non-compressible tissue, such as ligaments, that cannot be securely clamped by devices previously known in the art.

As described hereinbefore, clip 12 further comprises detents 51 of male locking member 50, each having an inwardly turned lip 55 on the top thereof and projecting toward flexible hinge 26. As best seen in FIG. 7, when clip 12 is moved to its closed position, lips 55 are positioned so as to further engage bifurcated recess 43, thereby providing an enhanced locking feature for greater latching strength and safety. As shown in FIG. 7, wherein clip 12 is in the closed position, but without tissue clamped between first and second legs 22 and 24, there is a noticeable gap G between lips 55 and the front wall of recess 43. As such, lips 55 are not engaging bifurcated recess 43, and therefore are not fully participating in the locking action of latch mechanism 14. However, when clip 12 is secured around a tissue, it forces second leg 24 upward, thereby flexing and shortening second leg 24. As second leg 24 shortens, gap G diminishes until lip 55 is engaged with the wall of recess 43, thereby providing the enhanced locking feature to clip 12. Thus, with the latch mechanism of clip 12, as the diameter or non-compressibility of a selected tissue increases, the latching action of clip 12 becomes greater. A prior art clip with conventional latch mechanism would fail long before clip 12 since it does not posses features that prevent the further shortening of one or more legs as the diameter of the selected tissue increases.

Prior art clips similar to clip 12 are described in detail in the commonly assigned U.S. Pat. No. 4,834,096 to Oh et al. and U.S. Pat. No. 5,062,846 to Oh et al., the disclosures of which are incorporated herein in their entireties. In addition, a particularly suitable clip is the HEM-O-LOK® clip commercially available from the assignee of the present invention. These clips are currently available in sizes designated "M", "ML", "L" and "XL". The clip cartridge described hereinbelow can be adapted to accommodate any sizes of HEM-O-LOK® clips commercially available.

Figure 8A:
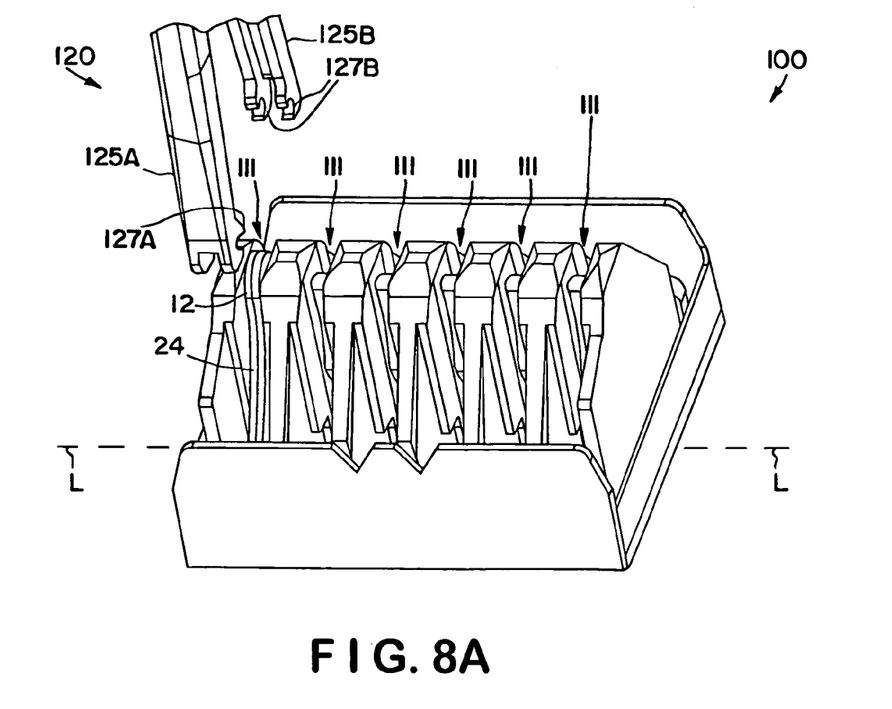
FIG. 8A is a perspective view of a clip applier being inserted into a compartment of a clip cartridge to engage a surgical ligating clip provided in accordance with the present invention.
Figure 8B:
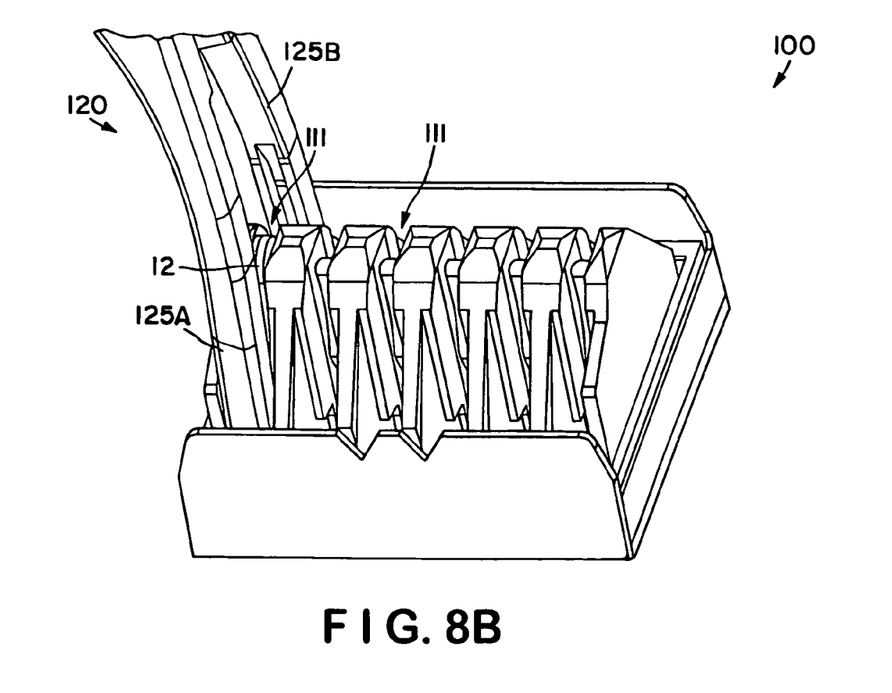
FIG. 8B is another perspective view showing the clip applier engaging the surgical ligating clip loaded in one of the compartments of the clip cartridge as shown in FIG. 8A.
Figure 8C:
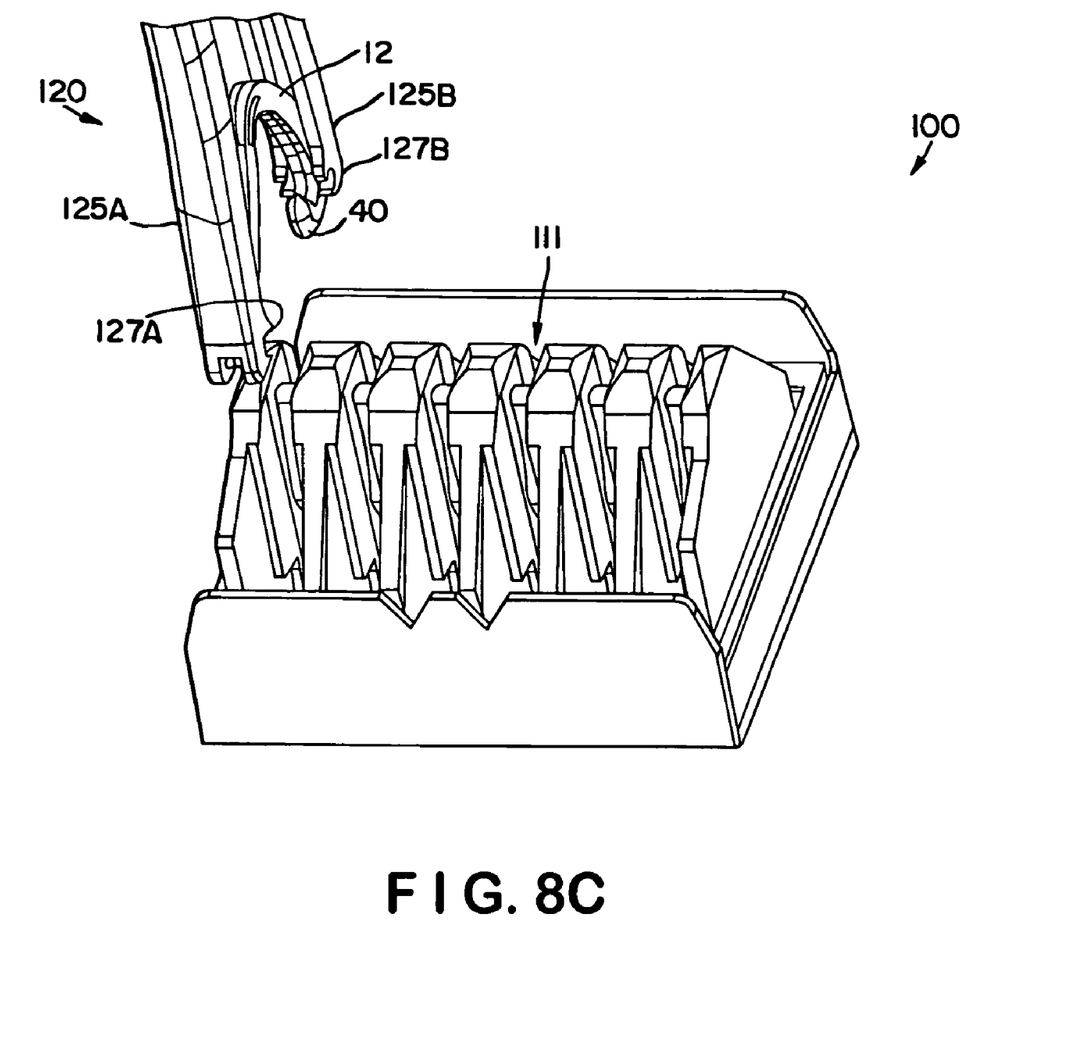
FIG. 8C is another perspective view showing the clip applier extracting the surgical ligating clip from the compartment of the clip cartridge shown in FIG. 8A.

Referring now to FIGS. 8A-8C, a preferred embodiment of a clip cartridge, generally designated 100, is shown for use with clip 12 of the present invention. Clip cartridge 100 preferably is constructed from a single-molded plastic body from which several features are formed. In particular, clip cartridge 100 comprises a plurality of clip retaining chambers or compartments 111 spaced along a longitudinal axis L of clip cartridge 100. Each clip compartment 111 is substantially identical and adapted for storing one clip 12, which preferably has an asymmetric design as described above and illustrated in FIGS. 1-7. FIG. 8A illustrates one clip 12 in a stored condition in one of clip compartments 111. It will be understood, however, that preferred embodiments of clip cartridge 100 include several clip compartments 111 for storing several clips 12. For instance, clip cartridge 100 is adapted for storing six clips 12, although other embodiments can be provided that store more or less clips 12. If desired, an adhesive backing (not shown) can be provided on the underside of clip cartridge 100 to facilitate securing clip cartridge 100 to a tray or other supporting component during use.

FIGS. 8A-8C also illustrate the distal end of a representative clip applying instrument for clip 12, generally designated 120, comprising opposing pivotable jaws 125A and 125B. Jaws 125A and 125B have respective jaw recesses 127A and 127B adapted to engage and retain bosses 56, 58, 62 and 64 of clip 12 (see FIGS. 1-6). According to a method provided by the invention, FIG. 8A illustrates clip applying instrument 120 in a position over clip 12 prior to inserting clip applying instrument 120 into a selected clip compartment 111. FIG. 8B illustrates clip-applying instrument 120 being inserted into selected clip compartment 111 to load clip 12 into locking engagement with clip applying instrument 120 (with bosses 56, 58, 62 and 64 retained in jaw recesses 127A and 127B). FIG. 8C illustrates the subsequent step of extracting clip 12 from clip cartridge 100 by removing clip applying instrument 120 with clip 12 loaded therein.

One advantage of clip 12 disclosed herein is that although clip 12 provides a superior redundant locking mechanism over the prior art, it does not require a specially-modified clip applying instrument 120 for application to the tissue. Rather, a standard clip applying instrument 120, such as is shown in FIGS. 8A through 8C, will work equally well with application of clip 12, as disclosed herein.

In the preferred embodiment of clip 12, as best shown in FIGS. 3 through 6, female locking member 40 of first leg 22 terminates at a sharp tip 68 with a cutting edge 49 extending at least along a portion of the length of the top surface of hook 41 and the distal end of second leg 24 includes a pair of sharp tissue-penetrating teeth 72 and 74. As first and second legs 22 and 24 are moved to the closed position, sharp teeth 72 and 74 on second leg 24 and sharp tip 68 and cutting edge 49 on first leg 22 stretch, puncture and cut through tissue adjacent to the tissue selected for clamping. This cutting action prevents surrounding tissue from being caught in latch mechanism 14 as clip 12 is closed, thereby ensuring proper locking of latch mechanism 14.

It will be understood that various details provided herein may be changed without departing from the scope of the presently disclosed material. Furthermore, the foregoing description is for the purpose of illustration only, and not for the purpose of limitation—the invention being defined by the claims.

What is claimed is:

1. A surgical clip with an interlocking latch mechanism, comprising:

a first leg and a second leg, each of said legs having an inner vessel-clamping surface and an outer surface, said inner surfaces being positioned in opposition to each other;

a flexible hinge section integrally disposed between and joining the proximal ends of said first and second legs; and a female locking member positioned on the distal end of said first leg and comprising a resilient inwardly turned hook defining a recess in a mouth of said hook, and a male locking member positioned on the distal end of said second leg comprising at least one detent extending therefrom, said female and male locking members being formed whereby when said first and second leg members are moved from an open position to a closed position about said hinge section, said resilient hook of said female locking member is urged open to receive the detent of said male locking member in the recess thereof so as to removably lock said first and second leg members of said surgical clip in said closed position; and further comprising a gusset within the mouth of said hook, wherein the at least one detent extending outwardly from said male locking member comprises two spaced-apart detents each having an inwardly turned lip extending generally toward said flexible hinge section for lockingly engaging said recess in the mouth of said hook.

2. The surgical clip according to claim 1, wherein said gusset divides said recess in the mouth of said hook so as to form a bifurcated recess.

3. The surgical clip according to claim 1, wherein said hinge section has a continuous concave inner surface and a continuous convex outer surface.

4. The surgical clip of claim 1, wherein said inner surface of said first leg has a concave radius of curvature between said hinge section and its distal end, said outer surface of said first leg has a convex radius of curvature between said hinge section and its distal end, said inner surface of said second leg has a convex radius of curvature between said hinge section and its distal end, and said outer surface of said second leg has a concave radius of curvature between said hinge section and its distal end.

5. The surgical clip according to claim 1, wherein at least one of said inner surfaces of said clip comprises a plurality of protrusions extending from said inner surface for providing improved vessel retention during and following closure of said clip.

6. The surgical clip of claim 5, wherein both of said inner surfaces of said clip comprise said plurality of protrusions.

7. The surgical clip of claim 1, further comprising a pair of bosses joined to opposite sides of said first leg between said hinge section and the distal end of said first leg, and a pair of bosses joined to opposite sides of said second leg at the distal end of said second leg.

8. The surgical clip of 7, wherein a portion of said pair of bosses joined to said first leg extend beyond said outer surface of said first leg to form a bridge section.

9. The surgical clip of claim 7, wherein said pair of bosses on said second leg each have a sharp tissue-penetrating tooth extending therefrom toward said first leg.

* * * * *